(12) United States Patent
Williams et al.

(10) Patent No.: US 8,952,198 B2
(45) Date of Patent: Feb. 10, 2015

(54) AMINATION PROCESS FOR MANUFACTURING AMINES USING CATALYST

(71) Applicants: Ian Williams, Park Ridge, NJ (US); John Christopher Williams, Hoboken, NJ (US); German Maya Maya-Hernandez, Irapuato (MX); Lilia Patricia Hernandez Salas, Irapuato (MX); Miguel Angel Lopez Guerrero, Valle De Santiago (MX)

(72) Inventors: Ian Williams, Park Ridge, NJ (US); John Christopher Williams, Hoboken, NJ (US); German Maya Maya-Hernandez, Irapuato (MX); Lilia Patricia Hernandez Salas, Irapuato (MX); Miguel Angel Lopez Guerrero, Valle De Santiago (MX)

( * ) Notice: Subject to any disclaimer, the term of this patent is extended or adjusted under 35 U.S.C. 154(b) by 0 days.

(21) Appl. No.: 13/815,078

(22) Filed: Jan. 30, 2013

(65) Prior Publication Data

US 2014/0213823 A1    Jul. 31, 2014

(51) Int. Cl.
*C07C 209/16* (2006.01)
*C07C 209/24* (2006.01)

(52) U.S. Cl.
CPC .................................. *C07C 209/24* (2013.01)
USPC ........... 564/480; 564/479; 544/358; 544/401; 544/402

(58) Field of Classification Search
CPC ............................ C07C 209/16; C07C 213/02
See application file for complete search history.

(56) References Cited

U.S. PATENT DOCUMENTS

| | | |
|---|---|---|
| 2,754,330 A | 7/1956 | Schreyer |
| 3,067,255 A | 12/1962 | Scholz et al. |
| 3,068,290 A | 12/1962 | Lictenberger et al. |
| 3,151,115 A | 9/1964 | Moss et al. |
| 3,520,933 A | 7/1970 | Adam et al. |
| 3,766,184 A | 10/1973 | Johansson et al. |
| 4,123,462 A | 10/1978 | Best |
| 4,209,424 A | 6/1980 | Le Goff et al. |
| 4,400,539 A | 8/1983 | Gibson et al. |
| 4,645,834 A * | 2/1987 | Dixon et al. ............. 544/106 |
| 4,720,588 A | 1/1988 | Turcotte et al. |

FOREIGN PATENT DOCUMENTS

GB          808114          1/1959

OTHER PUBLICATIONS

Barnes et al., Industrial & Engineering Chemistry Product Research and Development (1981), 20(2), p. 399-407.*
Satterfield, C. N. (1975), Trickle-bed reactors. AIChE J., 21: 209-228. doi: 10.1002/aic.690210202, p. 1.
Germain, A. et al., "Modeling a Trickle Bed Reactor: The hydrogenation of 2-Butanone on a Ruthenium Catalyst," ACS Symp Ser Int Symp on Chem React Eng, 5th, Mar. 13-15, 1978, n 65, Houston, TX, USA, p. 411-424 (Abstract only).
Gosselink, J.W. et al., "Simple Multicomponent Description of the Influence of the Particle and Pore Size of Commerical Catalysts on the Hydrodesulfurization of gas oil in small Trickle Flow Reactors," Chem Eng Process v 22 n 3 Nov. 1987 p. 157-162 (Abstract only).
Dudukovic, M.P. et al., "Multiphase Reactors: Models and Experimental Verification," Revue de L'Institut Francais de Petrole, 46(4), 439-465 (1991) (Abstract only).
Gianetto, A. et al., "Trickle-bed reactors. State of art and perspectives," Chemical Engineering Science First International Conference on Gas-Liquid and Gas-Liquid-Solid Reactor, Engineering Sep. 13-16, 1992, vol. 47, No. 13-14, Sep.-Oct. 1992 Columbus, OH, USA p. 3197-3218 (Abstract only).
Lemcoff, N.O. et al., "Effectiveness Factor of Partially Wetted Catalyst Particles: Evaluation and Application to the Modeling of Trickle Bed Reactors," Catalysis Reviews—science and Engineering—Catal Rev-Sci Eng Jan. 1988; 30 (3):393-456 (Abstract only).
Bradley, D., "what does my molecule look like?," Molecular Simulation, Scientific Computing World, Mar./Apr. 2002, 4 pages.
Gross, L. et al., "The Chemical Structure of a Molecule Resolved by Atomic Force Microscopy," Science, Aug. 28, 2009, vol. 325, No. 5944, pp. 1110-1114.
Zengmin, Transition Metal Catalysis, term paper for MSE 5317, Electronic Properties of Materials (Univ. Conn. 2009), http://electronics.wikidot.com/p-n-junction, 6 pages.

* cited by examiner

*Primary Examiner* — Brian J Davis
(74) *Attorney, Agent, or Firm* — Wiley Rein LLP

(57) ABSTRACT

Disclosed is a process for the preparation of an amine (particularly diamines and polyamines) by reacting an alkanolamine or a polyol with ammonia in the presence of a catalyst composed of two active metals from the group of transition metals, namely nickel and chromium supported on a microporous refractory substrate, in a hydrogenated, trickle bed reactor.

10 Claims, 2 Drawing Sheets

EDA MOLECULE MODEL

MAXIMUM OVERALL DIMENSION - 6 ANGSTROM UNITS

AMINATION PROCESS FOR MANUFACTURING AMINES USING CATALYST

CROSS REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, TABLE, OR COMPUTER PROGRAM LISTING COMPACT DISC APPENDIX

Not Applicable

BACKGROUND OF THE INVENTION

The present invention relates to catalytic amination of alkanolamines or glycols with ammonia to form diamines, polyamines, alkanolamines, and piperazine, or their derivatives by employing a catalyst composed of two active elements from the transition metal family, uniformly combined with a refractory microporous substrate. This process operates at lower temperatures and pressures than have hitherto been used.

A considerable number of methods for production of alkylamine products have been proposed and a number of them have been commercially utilized.

It is believed that two mechanisms are prominent in this process and they are: Reductive Amination and Heterogeneous Catalysis.

Reductive Amination: For ethylenediamine formation, the previous studies on ammonalysis of various alcohols is useful because alcohols such as ethanol and butanol are known to go via their corresponding aldehyde to primary, secondary and tertiary amines. Other studies have isolated the intermediate aldehyde (Pasek et al., 1972) (Baiker and Ridaz, 1977). The most direct evidence is by Bashirov (1971), who used isotope labeling to verify the mechanism.

Heterogeneous Catalysis: This is the straightforward reaction of —OH and —NH or $NH_2$ to form secondary or cyclic amines.

Reductive amination via catalytic hydrogenation of a mixture of aldehyde or ketone and ammonia leads to a predominance of primary amine when excess ammonia is present. At least five equivalents of ammonia should be used; smaller amounts result in formation of more secondary amine.

Various catalysts are manufactured and developed for amination of amines, some of which are discussed below:

U.S. Pat. No. 4,209,424 discloses a catalyst for implementing a process for manufacturing amines from alcohols composed of an active element in the transition metals family uniformly combined with a refractory porous structure with a specific surface of between 10 $m^2/g$ and 300 $m^2/g$ and with a pore diameter less than 5000 Å. A stabilizer in the form of a sodium-based compound with a sodium content of 0.15% to 20% by weight relative to the weight of the catalyst, and a promoter in the form of a rhodium-based compound with a maximum rhodium content of 0.1% by weight relative to the weight of the catalyst, may be associated with the active metal. The catalyst and the process are applicable to the ethanolamine-ammonia reaction with a view to producing ethylenediamine, piperazine, and useful byproducts. The amination reaction is carried out at 170° C. and 260° C.

U.S. Pat. No. 4,123,462 discloses nickel-rhenium catalyst and catalytic amination of lower aliphatic alkane derivatives such as alkanemono-ols, alkanediols and alcoholamines utilizing the said nickel-rhenium catalyst. The amination reaction is carried out at 125° C. to 350° C.

U.S. Pat. No. 7,601,875 discloses a process for the preparation of ethyleneamines by reacting monoethanolamine (MEOA) with ammonia in the presence of a catalyst in a reactor and separating the resulting reaction product, which comprises reacting ethylenediamine (EDA) obtained during the separation in a separate reactor in the presence of a catalyst to give diethylenetriamine (DETA), and the resulting reaction product is passed to the separation of the reaction product resulting from reactor. The reaction is carried out at temperature of 170° C. and a pressure of 200 bar.

U.S. Pat. No. 6,534,441 discloses a nickel/rhenium catalyst composition for the reductive amination of lower aliphatic alkane derivatives.

Process for production of ethylenediamine carried out by reacting ammonia with monoethanolamine in the presence of a catalyst at 200° C. to 500° C. in an atmosphere of an inert gas (e.g., nitrogen) according to demand is disclosed in Japanese Patent No. 3511666. The catalyst is prepared by heat-treating zeolite (e.g., mordenite) in an aqueous solution of EDTA, and has a high activity and a long service life.

U.S. Pat. No. 5,410,086 discloses a method for increasing the weight ratio of diethylenetriamine to piperazine at constant ethylenediamine conversion and constant space velocity in a process in which ethylenediamine and hydrogen are maintained in the presence of a hydrogenation catalyst, which method comprises increasing the hydrogen concentration in the liquid phase in an amount sufficient to effectuate control of the weight ratio of diethylenetriamine to piperazine in said process, and the catalyst is selected from nickel (Raney nickel), cobalt, or rhodium.

A number of production methods are utilized to produce the diamine and polyamine products and various catalysts are developed for these process. These processes, while generally employed throughout the industry, suffer from serious disadvantages.

The currently used processes for producing the products such as ethylenediamine, piperazine, aminoethylethanolamine, diethylenetriamine, aminoethylpiperazine, and hydroxyethylpiperazine are cumbersome, and a balance has to be struck between conversion-per-pass of the reactor, selectivity of the large volume products, and operating conditions. Generally if one increases conversion, selectivity decreases and more small-market yet high-value products are formed.

Further, these processes utilized for production of aforesaid products are carried out under extremely high pressures (200 kg/$cm^2$g) and temperatures (200° C.-254° C.), far above the critical pressure and temperatures of ammonia. These processes therefore are operating in the supercritical fluid region for ammonia which normally represents >80% of the volume flow to the reactor.

Therefore, there still exists a need in the art to develop a catalyst that helps in manufacturing high value product with higher selectivity, and at the same time carries out the process of amination at low temperature and pressure.

Therefore, it is an object of the present invention to provide a process of amination of alkanolamines or glycols with ammonia to form diamines, polyamines, and piperazine, or their derivatives.

Another object of this invention is to carry out the amination reaction at a pressure much lower than the critical pressure of ammonia and initiate the reaction at a temperature below the critical temperature of ammonia.

Yet another object of the present invention is to provide an amination catalyst to be employed in the process of amination of alkanolamines or glycols.

Another object of the present invention is to provide a process of amination having high yield and selectivity of diamines produced during the reaction.

BRIEF SUMMARY OF THE INVENTION

Therefore, in accordance with the above objectives, the present invention provides a process of catalytic amination of alkanolamines or glycols with ammonia to predominantly form alkylenediamines, said process comprising reacting said alkanolamines or glycols with ammonia in the presence of a catalyst comprising at least two active elements from the transition metals selected from cobalt, nickel, copper and chromium, uniformly allied to a refractory porous substrate with a specific surface area between 117 $M^2$/gm and 147 $M^2$/gm.

In another aspect the present invention provides the catalytic amination of alkanolamines or glycols with ammonia to form ethylenediamine (EDA); piperazine (PIP); diethylenetriamine (DETA); aminoethylpiperazine (AEP); aminoethylethanolamine (AEEA); hydroxyethylpiperazine (HEP); triethylenetetramine (TETA); and tetraethylenepentamine (TEPA).

DETAILED DESCRIPTION OF THE INVENTION

The present invention describes a process for the preparation of an amine using a catalyst composed of at least two active elements from the transition metals family and uniformly allied to a refractory porous substrate with a specific surface area.

Figure 2:
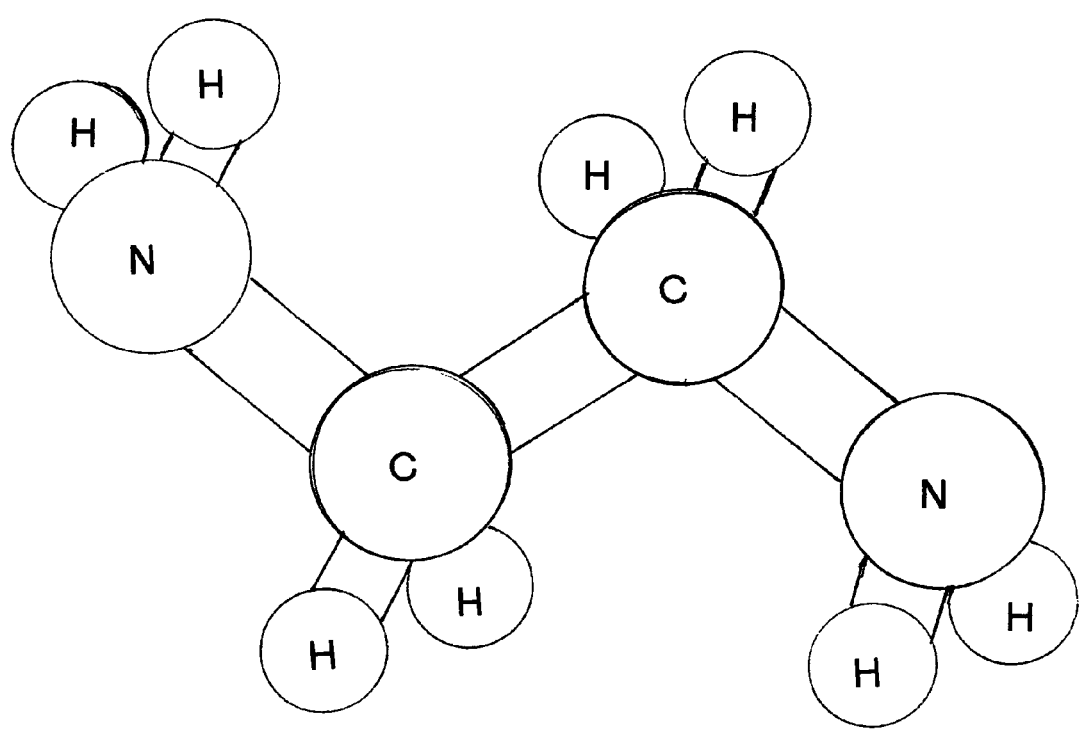
FIG. 2 illustrates the size of the EDA molecule.

In an embodiment, the present invention describes a process for the preparation of an amine by reacting an alkanolamine or a polyol with ammonia in the presence of a catalyst composed of two active metals from the group of transition metals consisting of cobalt, nickel, copper, and chromium; supported on a microporous refractory substrate with specific surface adequate for this reaction in minutes, and pore size capable of handling large molecules (see FIG. 2, the EDA molecule).

The transition metals are selected from cobalt, nickel, copper, and chromium, or their oxides. The preferred active metals are nickel and chromium, and the total transition metals content represents 60.0±10% of the total catalyst weight.

The microporous refractory substrate is selected from the group consisting of diatomaceous earth, graphite, alumina or alumina oxide, silica such as silica oxide, Kieselguhr, Attapulgite, thorium oxide, and cerium oxide. A specific diatomaceous earth is preferred.

In a preferred embodiment, the present invention provides the amination catalyst for use in the amination of an alkanolamine or glycol. The catalyst of the present invention comprises nickel and chromium metals deposited on a diatomaceous earth support. The nickel component is present in an amount of 49±5% wt. and the chromium component is present in an amount of 10±2% wt. The catalyst is activated by heating in a stream of hydrogen at 140° C.-200° C., at atmospheric pressure, for twelve hours or more.

The process for the preparation of an amine using amination catalyst in a heterogeneous phase for producing diamines, polyamines, alkanolamines, and piperazine, or their derivatives, exhibits high conversion and selectivity. Preferably, the present invention relates to use of the provided catalysts in a process for the preparation of diamines, polyamines, alkanolamines, and piperazine, or their derivatives, from polyols and/or alkanolamines.

In another embodiment, the present invention describes a process for the production of ethylenediamine, diethylenetriamine, piperazine, aminoethylpiperazine, aminoethylethanolamine, hydroxyethylpiperazine, and heavier amines, by reacting monoethanolamine and ammonia. Conversion per reactor pass is 50% or more and selectivity to ethylenediamine can be ≥65%.

In yet another embodiment, the present invention describes catalytic amination of alkanolamines or glycols with ammonia to form diamines, polyamines, and piperazine, or their derivatives, as well as alkanolamines using the aforementioned amination catalyst. The reaction is carried out at low pressure and temperature, i.e., well below the critical pressure of ammonia and below its critical temperature.

In another embodiment, the amination catalyst of the present invention is useful for production of predominantly monoethanolamine by reacting monoethylene glycol and ammonia at high nitrogen/carbon ratios such as 10:1.

The amination catalyst of the present invention is useful for the production of ethylene diamine, diethylenetriamine, piperazine, aminoethylpiperazine, aminoethyl ethanolamine, hydroxyethylpiperazine, and heavier amines by reacting monoethanolamine and ammonia. Further, the amination catalyst is also used for the production of predominantly monoethanolamine from monoethylene glycol and ammonia at high nitrogen/carbon ratios.

The amination catalyst of the present invention affords the conversion of >50% or more of the reactants per reactor pass and selectivity to ethylene diamine is ≥65% with high nitrogen/carbon ratios; and at low nitrogen/carbon mole ratios the conversion per reactor pass is ≥50% and the selectivity of conversion to higher amines exceeds 70%.

In the preferred embodiment, the present invention provides a method of producing diamines, triamines, amino alkanolamines, and piperazines using a nickel/chromium catalyst at a temperature of less than 130° C. and a pressure equal to or less than 50 Bar g.

In the most preferred embodiment, the present invention describes a method of producing ethylene diamine, diethylenetriamine, piperazine, aminoethylpiperazine, aminoethylethanolamine, hydroxyethylpiperazine, and heavier amines, by reacting monoethanolamine and ammonia using a nickel/chromium catalyst at a temperature of less than 130° C. and a pressure equal or less than 50 Bar. The process maintains conversions of greater than 50% and selectivity of greater than 65% EDA.

It is observed that minimizing the temperature and pressure of the reaction also minimizes the more complex reactions as many of the compounds were not detected during the reaction. The reaction products observed in reacting ethylene glycol or monoethanolamine with ammonia over the catalysts of the present invention were: ammonia ($NH_3$); ethyleneglycol (EG); monoethanolamine (MEA); ethylenediamine (EDA); piperazine (PIP); diethylenetriamine (DETA); aminoethylpiperazine (AEP); aminoethylethanolamine (AEEA);

hydroxyethylpiperazine (HEP); triethylenetetramine (TETA); and tetraethylenepentamine (TEPA).

These and other advantages of the invention may become more apparent from the examples set forth herein below. These examples are provided merely as illustrations of the invention and are not intended to be construed as a limitation thereof.

EXAMPLES

Many permutation and combination of metals and supports were tried in obtaining the selective Ni—Cr Catalyst, some of which are listed below:

TABLE 1

| Catalyst | Active Ingredient | Support | Form/ Surface Area |
|---|---|---|---|
| 1. | Nickel | CaO, Alumina $SiO_2$ | P/— |
| 2. | Nickel | Proprietary | E/— |
| 3. | Cobalt (25%) | Proprietary | E/— |
| 4. | Nickel (65%) | Proprietary | E/— |
| 5. | Cobalt | CaO, Aluminum SiO2 | P/65 $M^2/gm$ |
| 6. | Nickel (60%) | Proprietary | P/145 $M^2/gm$ |
| 7. | Nickel (60%) | SiO2, Attapulgite | E/— |
| 8. | Nickel | Al2O3 | P/— |
| 9. | Nickel (40%) | Kieselguhr | P/— |
| 10. | Nickel (68%) | Proprietary | P/125 $M^2/gm$ |
| 11. | Nickel | Proprietary | E/— |
| 12. | Nickel/Chromium Nickel (25-35%) Nickel Monoxide (25-35%) Chromium Oxide (10-15%) Graphite (1-5%) | Diatomaceous earth (25-35%) | P/130 $M^2/gm$ |

P = Pellets
E = Extrudates

When aminations were tried using the above range of catalysts, conversions ranged from zero to more than 50% and selectivity of EDA went from zero to 80%. The pressures used were between 71 psig (5 $Kg/cm^2G$) and 710 psig (50 $Kg/cm^2G$) and the reactor inlet temperature could be varied from 70° C. to 200° C. It was surprisingly found that for the catalyst of the present invention, the pressure range was narrowed to 500 psig to 710 psig and the temperature range from 70° C. to 130° C.

The reactor feed composition is extremely important to ensure good conversion and selectivity. It has been found that factors such as Temperature, Pressure, Contact Time, Nitrogen to Carbon Mole Ratio N/C, Water Content of Feed, and Hydrogen Content of Feed affects the conversion and product selectivity.

The amination process of the present invention is preferably carried out at temperatures between 90° C. and 130° C., and the pressures between 500 psig and 710 psig. Preferably, a contact time of 3 minutes to 7 minutes is sufficient. Contact time and N/C ratio are inter-dependent. For example, for a given mass flow of glycol or alkanolamine at high ammonia/alkyl (N/C) ratios, the contact time is less than at low ammonia to alkyl ratios. Water content of 10% or more in the feeds seems to enhance the speed at which ammonia gets into the liquid phase in order to undergo the reaction, hydrogen content of the vapor is about 40%-60%. Ammonia to alkyl ratios as high as 20 to 1 have been proposed in some patents, but it has been found that ratios in the range of 3:1 to 7:1 are adequate and result in very significant energy savings when the design of full scale plant is studied.

Figure 1:
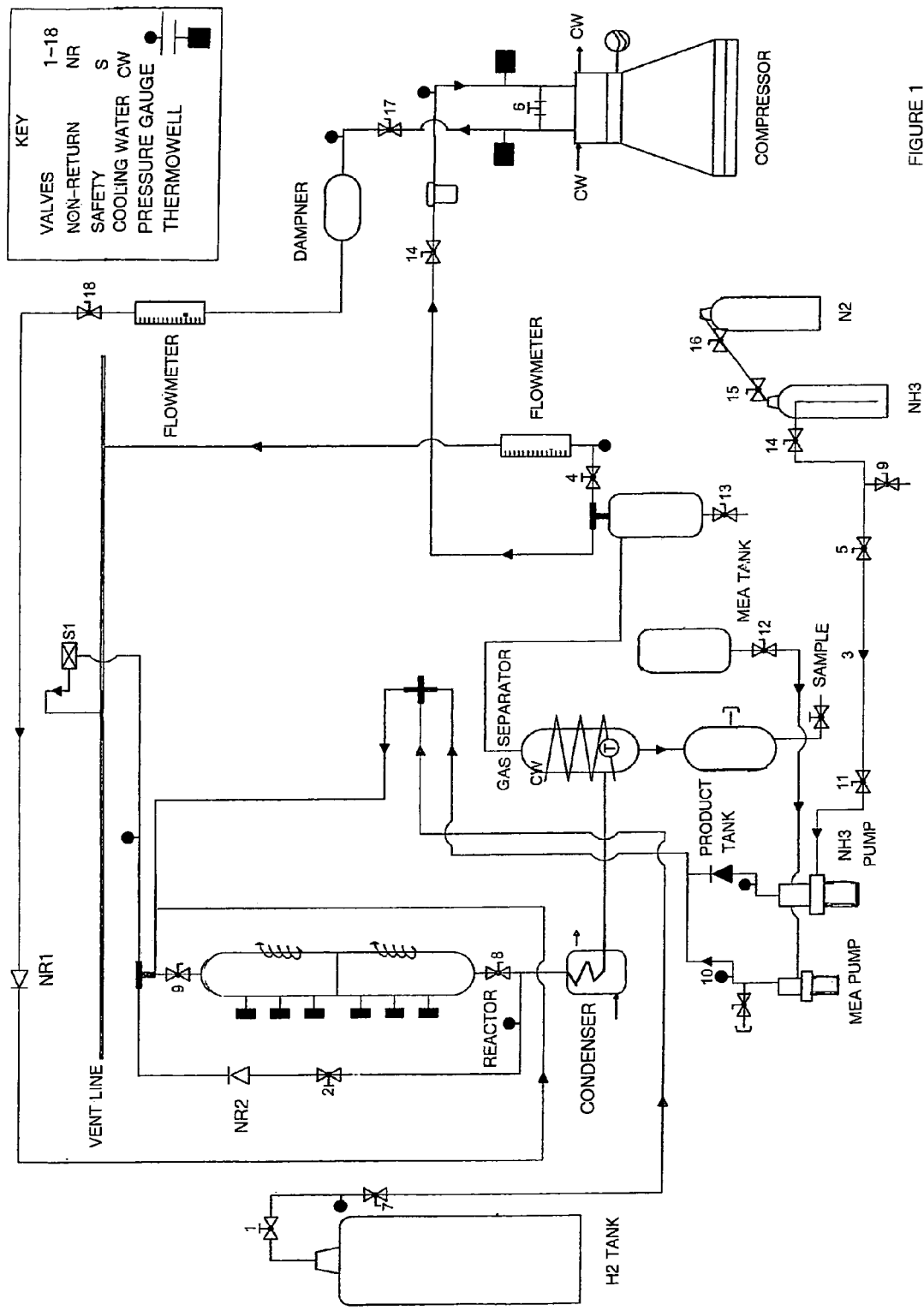
FIG. 1 illustrates a mini plant with MEA/MEG feed control.

The test reactor as in FIG. 1 is a mini plant with MEA/MEG feed control, $NH_1$ feed control, Hydrogen feed control, and collection of 100 percent of the product coming from the reactor.

COMPARATIVE EXAMPLES

TABLE 2

| Parameters | EXAMPLE 1 Catalyst 006 | | EXAMPLE 2 Catalyst 002 | | EXAMPLE 3 Catalyst 001 | | EXAMPLE 4 Catalyst 007 | | EXAMPLE 5 Catalyst 007 | | EXAMPLE 6 Catalyst 006 | |
|---|---|---|---|---|---|---|---|---|---|---|---|---|
| | A | B | C | D | E | F | G | H | I | J | K | L |
| MEA/H2O/NH3 mix feed rate ml/hr | 121 | 252 | 233 | 310 | 424 | 450 | 216 | 503 | 359 | 583 | 359 | 583 |
| NH3 Feed Rate ml/hr | 250 | 500 | — | — | — | — | — | — | — | — | — | — |
| H2 Feed Rate | 10 to 20 mole % feed | 10 to 20 Mole % feed | 10 to 20 mole % feed | 10 to 20 mole % feed | 10 to 20 mole % feed | 10 to 20 mole % feed | 10 to 20 mole % feed | 10 to 20 mole % feed | 10 to 20 mole % feed | 10 to 20 mole % feed | 10 to 20 mole % feed | 10 to 20 mole % feed |
| N/C Ratio | >3 | >3 | >3 | >3 | >3 | >3 | >3 | >3 | >3 | >3 | >3 | >3 |
| Reactor Temperature in ° C. | 159 | 191 | 152 | 176 | 168 | 151 | 189 | 173 | 164 | 187 | 153 | 167 |
| Reactor Temperature out ° C. | 161 | 194 | 158 | 179 | 172 | 157 | 197 | 189 | 167 | 192 | 154 | 184 |
| Reactor Pressure Kg/cm2g | 5.0 | 7.8 | 4.0 | 15.0 | 30.0 | 30.0 | 25 | 30 | 30 | 30 | 30 | 30 |
| Product Analysis | % Wt. | % Wt. | % Wt. | % Wt. | % Wt. | % Wt. | % Wt. | % Wt. | % Wt. | % Wt. | % Wt. | % Wt. |
| MEA | — | — | — | — | — | — | — | — | — | — | — | — |
| NH3 | — | — | — | — | — | — | — | — | — | — | — | — |
| H2O | — | — | — | — | — | — | — | — | — | — | — | — |
| EDA | 1.27 | 0.68 | 0.08 | 0.04 | 0.05 | 0.4 | 0.31 | 0 | 0.07 | 0.09 | 1.1 | 1.54 |
| PIP | 2.54 | 7.44 | 0.97 | 0.00 | 0.47 | 1.64 | 0.18 | 0 | 2.87 | 0.74 | 2.21 | 1.62 |
| DETA | — | — | — | — | — | — | — | — | — | — | — | — |
| AEP | — | — | — | — | — | — | — | — | Higher Amines | Higher Amines | — | — |
| AEEA | — | — | — | — | — | — | — | — | Prominent | 3.42 percent | — | — |
| HEP | — | — | — | — | — | — | — | — | | | — | — |
| X | — | — | — | — | — | — | — | — | 9.81 percent | | — | — |

TABLE 2-continued

| Conversion % | 25 | High | 1 | Low | Low | Low | Low | Low | High | Low | 18 | 15 |
|---|---|---|---|---|---|---|---|---|---|---|---|---|
| Seletivity % EDA/EDA + PIP | 33 | 9 | 7.6 | — | — | — | — | — | Low | Low | 33 | 49 |

| | EXAMPLE 7 Catalyst 12 | | EXAMPLE 8 Catalyst 0012 | | EXAMPLE 9 Catalyst 0012 | | EXAMPLE 10 Catalyst 0012 | |
|---|---|---|---|---|---|---|---|---|
| Parameters | M | N | O | P | Q | R | S | T |
| MEA/H2O/NH3 mix feed rate ml/hr | 336 | 384 | 384 | 384 | 384 | 384 | 384 | 384 |
| NH3 Feed Rate ml/hr | 1080 | 900 | | | 540 | 540 | Not Determined | Not Determined |
| Recycle Gas Feed Rate | 4.0 | <10.0 | Recycle | Recycle | Recycle | Recycle | <10 ALPH | <10 ALPH |
| H2 Feed Rate | 1.0 | 1.0 | 10-20 Mole % Feed | 10-20 Mole % Feed | 10-20 Mole % Feed | 10-20 Mole % Feed | 1 NM$^3$/Hr | 1 NM$^3$/Hr |
| N/C Ratio | >5 | Approx. 3 | >3 | >3 | >3 | >3 | <2 | <2 |
| Reactor Temperature in ° C. | 109 | 103 | 80 | 100 | 103 | 94 | 92 | 107 |
| Reactor Temperature out ° C. | 127 | 110 | 90 | 115 | 130 | 119 | 109 | 127 |
| Reactor Pressure Kg/cm2g | 35 | 35 | 35 | 35 | 45 | 45 | 35 | 35 |
| Product Analysis | — | — | — | — | — | — | — | — |
| MEA | 36.19 | 25.52 | — | — | 24.58 | 38.76 | 35.83 | 23.31 |
| NH3 | 24.05 | 49.29 | — | — | — | — | 13.9 | 20.36 |
| H2O | 24.15 | 13.09 | — | — | 40.5 | 26.91 | 25.1 | 22.19 |
| EDA | 10.2 | 9.66 | 6.5 | 18.22 | 13.07 | 7.70 | 4.4 | 8.44 |
| PIP | 2.44 | 1.51 | 0.6 | 1.04 | 3.09 | 0.26 | 10.0 | 11.58 |
| DETA | 0.35 | 0.49 | <3.0 | <2.0 | 2.34 | 1.11 | 2.54 | 4.36 |
| AEP | ND | ND | <3.0 | <2.0 | 1.07 | 0.24 | 0.76 | 2.43 |
| AEEA | ND | ND | <3.0 | <2.0 | 1.27 | 1.25 | 4.43 | 2.77 |
| HEP | 0.60 | 0.45 | — | — | 0.38 | 0 | 0.53 | 0.61 |
| X | ND | ND | — | — | 0.4 | 0.10 | — | — |
| TETA | — | — | — | — | — | — | 1.74 | 2.35 |
| TEPA | — | — | — | — | — | — | 1.35 | 0.73 |
| Conversion % | | | 24% | 52% | 50 | 23 | 50 | 23 |
| Seletivity % EDA/EDA + PIP | | | 91% | 95% | 80.9 | 95 | 80.9 | 95 |

From the above examples it was concluded that:
1. Example 8 utilizing the catalyst of the present invention shows 91% to 95% selectivity of EDA/EDA + PIP and approximate 52% conversion. FIG. 3 shows the MEA conversion vs. Selectivity at 110° C. and FIG. 4 shows MEA conversion vs. Selectivity at 90° C.
2. Example 9 utilizing the catalyst of the present invention shows 80.9% to 95% selectivity of EDA/EDA + PIP and approximate 50% conversion. FIG. 5 shows MEA conversion vs. Selectivity at 103-130° C. and 94-119° C.
3. Example 10 utilizing the catalyst of the present invention shows 80.9% to 95% selectivity of EDA/EDA + PIP and approximate 50% conversion.

From the above examples, it was concluded that:

Example 8 utilizing the catalyst of the present invention shows 91% to 95% selectivity of EDA/EDA+PIP and approximate 52% conversion. Lane P shows the MEA conversion vs. Selectivity at 100° C.-115° C., and Lane O shows MEA conversion vs. Selectivity at 80° C.-90° C.

Example 9 utilizing the catalyst of the present invention shows 80.9% to 95% selectivity of EDA/EDA+PIP and approximate 50% conversion. Lanes Q and R show MEA conversion vs. Selectivity at 103° C.-130° C. and 94° C.-119° C., respectively.

Example 10 utilizing the catalyst of the present invention shows 80.9% to 95% selectivity of EDA/EDA+PIP and approximate 50% conversion.

What is claimed is:

1. A process for the preparation of diamines and polyamines, comprising reacting an alkanolamine or a polyol with ammonia in the presence of hydrogen in a trickle bed catalytic reactor containing a nickel/chromium catalyst on a support material, operating at a pressure less than 55 kg/cm$^2$g.

2. The process as claimed in claim 1, wherein the diamine or polyamine is selected from the group consisting of ethylene diamine, diethylenetriamine, piperazine, aminoethylpiperazine, aminoethyl ethanolamine, and hydroxyethylpiperazine.

3. The process as claimed in claim 1, wherein the diamine is predominantly ethylene diamine.

4. The process as claimed in claim 1, initiated at a temperature in the range of 110° C. to 130° C.

5. The process as claimed in claim 1, wherein metal content of said catalyst represent about 60.6±10% of the total catalyst weight.

6. The process as claimed in claim 1, wherein said support material is a microporous refractory substrate selected the group consisting of from silica, alumina, diatomaceous earth, and graphite.

7. The process as claimed in claim 1, wherein said catalyst is composed of 50% wt. of nickel and 10.6% wt. of chromium supported on a microporous refractory substrate comprising less than 40% wt. of diatomaceous earth.

8. The process as claimed in claim 1, wherein about 98% of the catalyst has a pore volume wherein the pores have a diameter larger than the molecule hydroxyl ethylpiperazine, but less than 100 nanometers.

9. The process as claimed in claim 1, wherein the reacting in the trickle bed catalytic reactor is carried out for between 3 to 7 minutes.

10. The process as claimed in claim 1, wherein the alkanolamine is monoethanolamine in the presence of about 10% wt. water content.

* * * * *